US00PP12541P2

(12) United States Plant Patent
Kaskel

(10) Patent No.: US PP12,541 P2
(45) Date of Patent: Apr. 9, 2002

(54) HEMEROCALLIS PLANT NAMED 'SOUTHERN SPARKLE'

(75) Inventor: Mathew Kaskel, Homestead, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 0 days.

(21) Appl. No.: 09/657,543

(22) Filed: Sep. 8, 2000

(51) Int. Cl.[7] ..... A01H 5/00
(52) U.S. Cl. ..... Plt./312
(58) Field of Search ..... Plt./312

*Primary Examiner*—Bruce R. Campell
*Assistant Examiner*—June Hwu
(74) *Attorney, Agent, or Firm*—Foley & Lardner

(57) ABSTRACT

A new and distinct cultivar of Hemerocallis named 'Southern Sparkle' characterized by its pastel yellow flowers with a contrasting red eye-zone which are borne on tall branched scapes. The flowers do not fade in warm, bright conditions and are resistant to water spotting. Plants of 'Southern Sparkle' bloom early in the season, and then repeatedly through out the growing season. Plants of 'Southern Sparkle' are evergreen, thus they are attractive in landscapes. The plant grows vigorously, and propagates easily by division or tissue culture.

2 Drawing Sheets

SUMMARY OF THE INVENTION

The present invention relates to a new and distinct cultivar of Hemerocallis plant, hereinafter referred to by the cultivar name 'Southern Sparkle'. The genus Hemerocallis is a member of the family Liliaceae.

Hemerocallis comprises a genus of approximately 15 species of clump-forming herbaceous perennials which are native to central Europe, China and particularly Japan. The flowers of Hemerocallis are lily-like and are borne in succession atop tall, frequently branched scapes. Individual flowers last one day, this Hemerocallis are commonly known as 'Daylily' in the commercial trade.

In recent years Hemerocallis has been extensively hybridized, and many named cultivars exist. Hemerocallis hybrids are hardy spring and summer blooming plants which are particularly well adapted to landscape plantings. The plants form clumps of fan-shaped crowns of vertically ranked, keeled, strap-like leaves. Plants (individual crowns) range in size from approximately 20 cm to over 90 cm in spread. Depending upon the parentage, Hemerocallis hybrids may be deciduous, evergreen or semi-evergreen.

Hemerocallis hybrids come in a range of colors including, orange, yellow, pink, reddish, or purplish. The flowers are funnel-shaped or campanulate with six segments joined at the base into a tube.

Asexual propagation of Hemerocallis is frequently done by division. Propagation can also be done through the use of tissue culture practices.

The new cultivar 'Southern Sparkle' is a product of a planned breeding program and was originated by the inventor Matthew Kaskel from a cross made during such a program in Homestead, Fla. in April, 1994. The parent plants were each seedlings of Hemerocallis×hybrid. Neither parent is patented. The male and female parents were proprietory Hemerocallis selections. The selection comprising the new variety was chosen after commencement of flowering of the progeny in April of 1995 and was originally identified by the number code #95-23. After more thorough commercial evaluation, the cultivar was given the name 'Southern Sparkle'.

Asexual reproduction by tissue culture of the new cultivar by the inventor in the laboratories of Twyford Plant Laboratories, Inc., in Homestead, Fla., has demonstrated that the combination of characteristics as herein disclosed for the new cultivar 'Southern Sparkle' are firmly fixed, reproduces true to type, and are retained through successive generations of asexual reproduction.

BRIEF DESCRIPTION OF THE DRAWINGS

The accompanying color photographic illustrations show typical characteristics of Hemerocallis 'Southern Sparkle,' with colors being as nearly true as possible with illustrations of this type.

Sheet 1 shows a 10-month-old plant of 'Southern Sparkle' grown from tissue culture and flowering in a 15 cm pot.

Sheet 2 is a close-up view showing the characteristics of the flowers and scape.

SPECIFIC DESCRIPTION OF THE NEW VARIETY

The following observations, measurements and values describe plants grown in Apopka, Fla., under field conditions which closely approximate those generally used in horticultural practice. Color references are made to The Royal Horticultural Society (R.H.S.) Colour Chart, except where general terms of ordinary significance are used.

The following traits have been repeatedly observed and are determined to be basic characteristics of 'Southern Sparkle' which in combination distinguish this Hemerocallis as a new and distinct cultivar:

1. Flowers are pastel yellow with a red eye-zone.
2. Flowers do not fade in warm, bright conditions and are resistant to water spotting.
3. Individual scapes are tall and branched with many buds which open in succession for approximately 4 weeks. Subsequent scapes develop quickly after the initial scapes flower out.

4. Spent flowers of 'Southern Sparkle' shrivel, become inconspicuous, drop from the scape quickly, and do not interfere with the opening of subsequent flowers.
5. Plants of 'Southern Sparkle' begin blooming very early in the season (April), and rebloom throughout a 90-day bloom season.
6. Plants of 'Southern Sparkle' are growing vigorously and propagate readily by division and tissue culture.
7. Plants of 'Southern Sparkle' have narrow evergreen foliage making them attractive in landscapes even when not in bloom.

The petal colors and eyezone colors are more intense in 'Southern Sparkle' than in either of the two parents. Additionally, 'Southern Sparkle' is more floriferous and more highly recurrent than either of the two parents.

'Southern Sparkle' has not been observed under all possible environmental conditions. The phenotype may vary significantly with variations in environment such as temperature, light intensity, day-length and humidity, without, any change in genotype. The plants were 10 months old when described, and derived from a tissue culture plantlet.

CLASSIFICATION

Commerical: Hemeorcallis cv. 'First Spring'.

Parentage:

*Male parent.*—Proprietary selection of Hemerocallis.

*Female parent.*—Proprietary selection of Hemerocallis.

Genus/species: Hemerocallis×hybrid.

Propagation: Vegetative, by tissue culture.

Plant:

*Form/growth habit.*—Clump-forming; Fan-shaped crowns of vertically ranked, opposite, smooth, keeled, ligulate leaves.

*Height.*—Approximately 50 cm to 60 cm including inflorescence.

*Width.*—Approximately 45 cm to 60 cm.

Foliage:

*Size.*—The mature leaves are approximately 45 cm to 55 cm long, and 1.8 to 2.2 cm wide (flattened for measurement).

*Shape.*—The leaf blade is ligulate with an acute tip. The margins are entire. The leaves are curved over their length. The leaf is keeled, and arched downward.

*Surface texture.*—The leaf blade is thin, with a smooth surface.

*Color.*—The leaves are medium green throughout. The upper surfaces are greener than, but closest to 137 A, and lower surfaces are between 137 A and 137 B. The margins of the leaf bases may be flushed and striated with 184 D.

*Average number.*—Plant produces approximately 6 pairs of leaves before producing an inflorescence.

*Dormancy.*—Plants of 'Southern Sparkle' are evergreen, and require no dormant period. If grown in appropriate conditions, plants of 'Southern Sparkle' are capable of growing year round. If grown in locations with freezing winter conditions, plants of 'Southern Sparkle' will become dormant and loose their leaves.

Inflorescence:

*Borne.*—Flowers borne in succession, with new buds opening daily, atop a 3 or 4 branched scape. Scapes may produce approximately 12–20 buds, with each branch having 3–4 buds each.

*Shape.*—The inflorescence is an upright terminally branched determinant panicle.

*Buds.*—Dimensions: Approximately 6.8 cm long and 1.90 cm in width. Color: Yellow orange between RHS 22 C and RHS 22 D, striated with between RHS 146 C and RHS 146 D with green 146 B sepal tips.

*Individual flowers.*—Dimension: The diameter of the flower is approximately 9.0 cm to 10.1 cm (not flattened). The depth of the flower is between 5.5 cm and 6 cm. The sepals and petals are reflexed outward. There are three sepals and three petals, with cuspidate apex. The sepals are approximately 7.3 cm long 3.3 cm wide, and are ovate in shape. The petals are approximately 7.0 cm long, 4.9 cm wide, and are obovate in shape. Individual flower parts flattened for measurement. Shape: Funnel-form to campanulate, segments ovate or obovate and moderately reflexed. Petals ruffled along the margins. Sepals wavy along the margins.

*Colors.*— Upper Surface: Sepals have three distinct zones of color: Yellow-orange 18 A, tinged with 178 D (eye zone). Base of sepal (throat) 145 A. Petals have three distinct zones of color: Yellow-orange 18 A, and between RHS 178 A and RHS B (eye zone). Base of petals (Throat): 145 A. Lower-Surface: Sepals yellow-orange 18 A, striated with 145 A. Base of Sepal: 145 A. Tip of sepal 145 A. Petals yellow-orange between RHS 16 B and RHS 16 C. Base of petals: 145 A.

*Texture.*—Moderately thick, leathery texture.

*Quantity.*—Approximately 12–20 flowers/buds present depending on the size of plant and inflorescence. Branch spikes contain approximately 3 to 4 flowers/buds.

*Senescent flower.*—Spent flowers collapse and shrivel, becoming inconspicuous, eventually falling from the scape in 1 or 2 days.

*Scape.*—The scape is approximately 50 cm to 60 cm in height, and 8 mm in diameter measured at midpoint and darker than, but closest to 137 B in color.

*Bracts.*—Small leaf-like bracts are present at the junctions of the branches and the scape and the flower buds and the scape. The bracts are variable in size, 2.5 cm to 11 cm long and are between RHS 137 B and RHS 137 C in color on both surfaces of the bracts.

*Time of blooming.*—In mature plants, flowering begins approximately very early season (March 15 as observed in Apopka, Fla.).

*Duration of blooms.*—Individual flowers last 1 day, and the total duration of flowering is about 90 days with subsequent scapes appearing through out the growing season.

*Fragrance.*—Slight.

Reproductive organs:

*Ovary.*—Superior oblong, 9 mm in length, 5 mm wide. Color: between RHS 146 B and RHS 146 C.

*Pistil.*—One pistil per flower. 8.9 cm long, style 2.0 mm wide. Color: yellow between RHS 10 B and RHS 10 C tinged with 146 D at base.

*Stamens.*—Six present, Filament 4.9 cm long, flat curved 2 mm wide, yellow 10 B tinged with 146 D at base.

*Anthers.*—8 mm long, brown-black, closest to RHS 200A.

*Pollen.*—21 A.

Fruit: A three valved, loculicidal capsule 2.4 cm wide, and 3 cm in height. Color varies between RHS 137 B and RHS 137 C, becoming tinged with yellow RHS 20 C when ripe. Each chamber contains approximately 3 to 6 seeds, 4 mm to 7 mm and mostly round, but often oblong.

Seed characteristics: Capable of producing viable seed.

Roots: Very thick fleshy white roots with fine laterals.

Cultural:

*USDA zone.*—Grows and blooms best when grown in USDA Zones 6 to 11.

*Diseases/pests.*—No particular sensitivity to pests or diseases has been observed. Aphids may infest plants during the winter months.

I claim:

1. A new and distinct cultivar of Hemerocallis plant named 'Southern Sparkle' as illustrated and described.

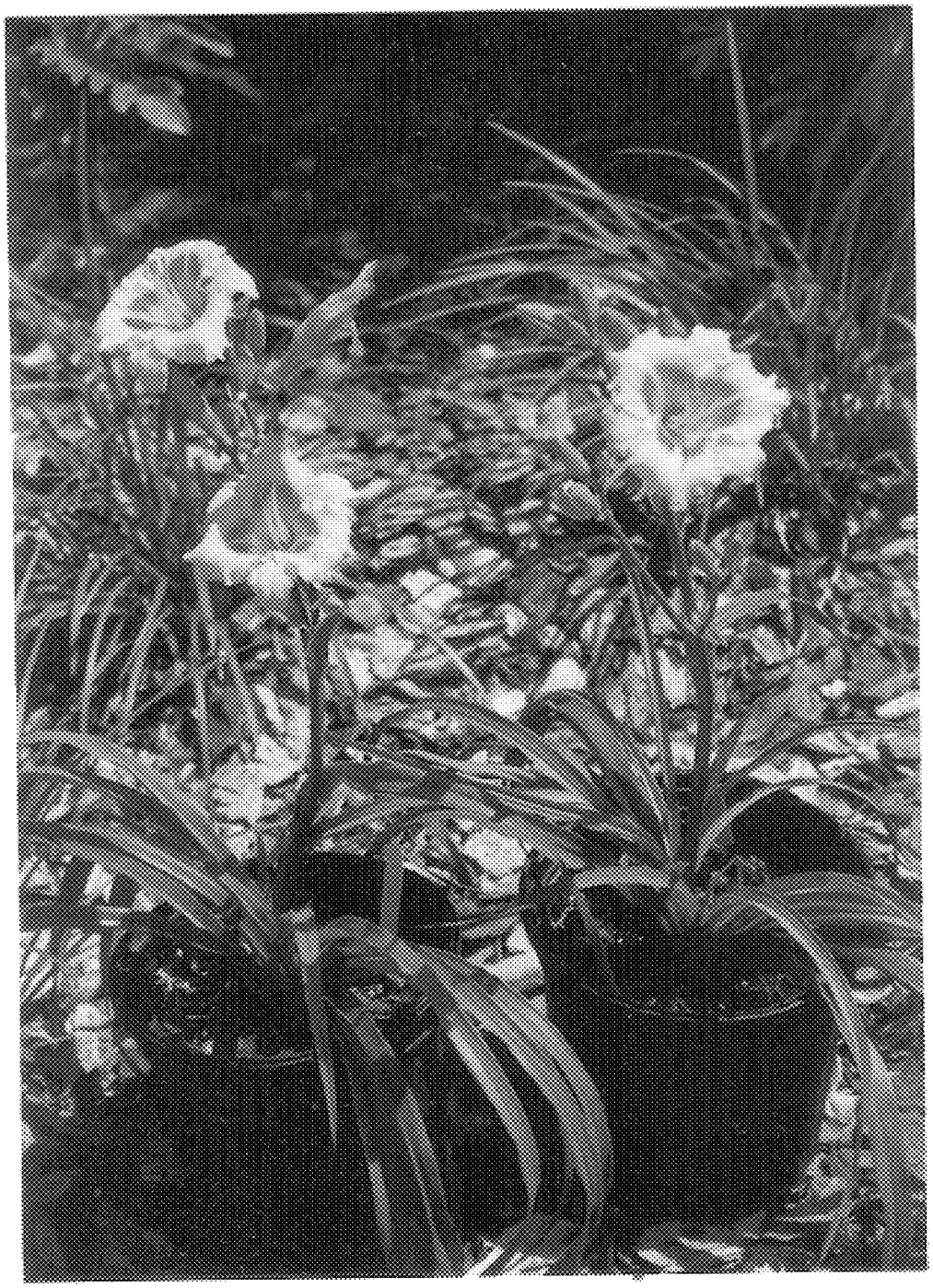

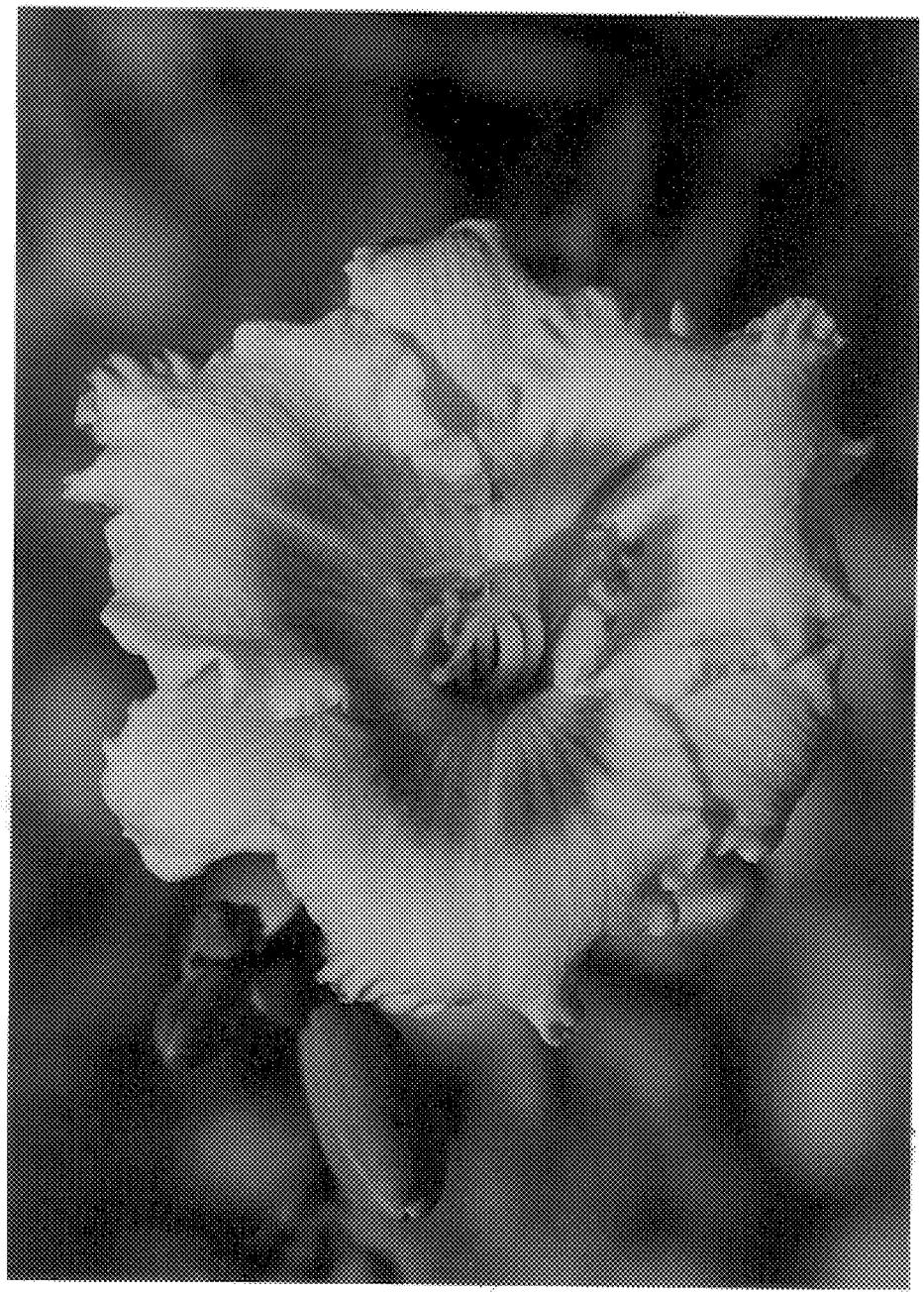

* * * * *